United States Patent
Pfeiffer et al.

(10) Patent No.: US 7,368,586 B2
(45) Date of Patent: May 6, 2008

(54) ORGANOSILICON COMPOUNDS WITH A MASKED ISOCYANATE GROUP

(75) Inventors: Jürgen Pfeiffer, Burghausen (DE); Torsten Gottschalk-Gaudig, Mehring (DE); Thomas Kornek, Burghausen (DE); Volker Stanjek, München (DE); Alfred Popp, Unterhaching (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/668,207

(22) Filed: Jan. 29, 2007

(65) Prior Publication Data

US 2007/0123644 A1    May 31, 2007

Related U.S. Application Data

(63) Continuation of application No. PCT/EP2005/007079, filed on Jun. 30, 2005.

(30) Foreign Application Priority Data

Jul. 29, 2004    (DE) .................. 10 2004 036 721

(51) Int. Cl.
*C07F 7/10* (2006.01)
*C07F 7/18* (2006.01)
(52) U.S. Cl. .................. 556/419; 556/418; 556/420; 556/421
(58) Field of Classification Search .............. 556/419, 556/418, 420, 421
See application file for complete search history.

(56) References Cited

U.S. PATENT DOCUMENTS

| 4,036,813 A | 7/1977 | Hardman et al. |
| 2002/0016486 A1 | 2/2002 | Pinske |

FOREIGN PATENT DOCUMENTS

| DE | 3424534 A1 | 1/1986 |
| DE | 102 40 388 A1 | 3/2003 |
| EP | 212 058 B1 | 1/1990 |
| JP | 8-291186 | 11/1996 |
| JP | 10067787 A | 3/1998 |

OTHER PUBLICATIONS

Landon et al., Pitture e Vernici Europe, 73(11), 1997, pp. 18-24 (abstract only).*
Patbase Abstract corresponding to DE 10240388 A, 2003.
Patbase Abstract corresponding to DE 3424534 A, 1986.
Patbase Abstract corresponding to EP 0212058 B, 1990.
Patent Abstract of Japan corresponding to JP 08-291186 A, 1996.
Patent Abstract of Japan corresponding to JP 10-067787 A, 1998.
D.A. Wicks, Z.W. Wicks, Prog. Org. Coat. 1999, 36, pp. 148-172.
H. Bach, C. Gürtler, S. Nowak, Farbe & Lack Dec. 2003, 109, pp. 32-42.

* cited by examiner

*Primary Examiner*—Elvis O. Price
(74) *Attorney, Agent, or Firm*—Brooks Kushman P.C.

(57) ABSTRACT

Blocked silyl isocyanates contain a methylene group between the blocked isocyanate group and silicon. The blocked isocyanates are easily prepared in high yield and purity.

10 Claims, No Drawings

ORGANOSILICON COMPOUNDS WITH A MASKED ISOCYANATE GROUP

CROSS-REFERENCE TO RELATED APPLICATIONS

This application is a continuation of PCT application Ser. No. PCT/EP2005/007079, filed Jun. 30, 2005, to which priority is claimed, and which claims the benefit of German Application No. 10 2004 036 721.3, filed Jul. 29, 2004, to which priority is also claimed.

BACKGROUND OF THE INVENTION

1. Field of the Invention

The present invention relates to organosilicon compounds having an isocyanate group which is masked by a blocking agent, to processes for preparing them, to processes for eliminating the blocking agents, and to the use of the organosilicon compounds.

2. Background Art

Organofunctional silanes, i.e., compounds which contain an organic functional group as well as a silyl group, have acquired industrial significance in a wide variety of applications, for example as adhesion promoters, as crosslinkers, and for modifying surfaces. Of particular importance in this context is the isocyanate functionality, which on account of its high reactivity toward protic compounds such as alcohols, amines, oximes and the like, is able to react in diverse ways.

Frequently, however, when isocyanates are used in an aqueous environment or in isocyanate-crosslinking one-component paint systems, a masked form of an isocyanate is required in order to prevent unwanted premature reaction of the isocyanate. For this purpose use is frequently made industrially of isocyanates whose isocyanate group has been blocked with a moiety which is thermally facile (D. A. Wicks, Z. W. Wicks, PROG. ORG. COAT. 1999, 36, 148-172). These blocked isocyanates masked by a blocking agent are frequently easy to prepare and, furthermore, exhibit a markedly reduced toxicity in comparison to that of the corresponding free organic isocyanate.

Some organosilicon compounds containing masked isocyanate groups are known, for example from DE 34 24 534 A1, EP 0 212 058 B1, JP 08 291186 and JP 10 067787. Common to all of these compounds, however, is the fact that between the masked isocyanate group and the silyl group there is a propylene group, as a result of which the reactivities with respect to hydrolysis and condensation are comparatively low. As a consequence, relatively high temperatures are frequently necessary for the reaction of these compounds, which leads in turn to the blocking agent being eliminated at an unwanted point in time. As a result, these compounds are totally unsuitable for many applications, or at least have great disadvantages.

SUMMARY OF THE INVENTION

An object of the invention was therefore to provide organosilicon compounds which carry masked isocyanate groups but have high reactivity with respect to hydrolysis and condensation, and also to provide processes for preparing and using them. These and other objects are surprisingly achieved by blocked isocyanates linked to silicon via a methylene group.

DETAILED DESCRIPTION OF THE PREFERRED EMBODIMENT(S)

The invention provides organosilicon compounds of the general formula (I)

$$(RO)_{3-n}(R^1)_n Si\text{—}CH_2\text{—}N(H)\text{—}C(O)\text{—}X \qquad (I),$$

where

R is a $C_1$-$C_{15}$ hydrocarbon radical or an acetyl radical, $R^1$ is a hydrogen atom or an Si—C-bonded $C_1$-$C_{20}$ hydrocarbon radical which is unsubstituted or substituted by —CN, —NCO, —NR$_2$, —COOH, —COOR, -halogen, -acryloyl, -epoxy, —SH, —OH or —CONR$_2$ and in which in each case one or more nonadjacent methylene units can be replaced by groups —O—, —CO—, —COO—, —OCO—, or —OCOO—, —S—, or —NR—, and in which one or more nonadjacent methane units can be replaced by groups —N=, —N=N—, or —P=, n is 0, 1 or 2, X is a group —NR$^2$R$^3$, —S—R$^5$, —C(H)(CO$_2$R$^5$)$_2$, or —O—N=CR$^2$R$^3$, $R^2$, $R^3$ and $R^5$ have the definitions of $R^1$, or are a cyclic, optionally branched hydrocarbon radical having 2-30 carbon atoms with at least 3 ring atoms, which is optionally functionalized by one or more groups —O—, —CO—, —COO—, —OCO—, —S—, =N—, —NR$^1$—, and —CONR$^1$—.

On thermal exposure of the organosilicon compounds of the general formula (I), the respective blocking agent HX is eliminated, and free isocyanate groups are generated. Mechanisms for eliminating the blocking agents HX, and suitable elimination temperatures and methods of determining them are known to the skilled worker from, for example, D. A. Wicks, Z-W. Wicks, PROG. ORG. COATINGS, 1999, 36, 148-172 or H. Bach, C. Gürtler, S. Nowak, FARBE & LACK 12/2003, 109, 32-42.

The elimination temperature can be influenced by catalysts such as bismuth compounds, tin compounds, or amines, if desired.

The elimination of the blocking agent HX from the organosilicon compounds of the general formula (I) that contain blocked isocyanate groups preferably takes place in a temperature range of 30-250° C., more preferably 50-180° C., and most preferably in a temperature range of 80-150° C. The blocking agents HX which are thermally eliminatable preferably have molecular weights M <500, and more preferably M<200.

The invention also provides a process for eliminating the blocking agents HX from the organosilicon compounds of the general formula (I) in a temperature range of 30-250° C.

Preferably R are $C_1$-$C_8$ hydrocarbon radicals, more preferably $C_1$-$C_3$ alkyl radicals, especially methyl, ethyl or acetyl radicals; $R^1$ are preferably $C_1$-$C_8$ hydrocarbon radicals, more preferably $C_1$-$C_3$ alkyl radicals, and especially the methyl and ethyl radicals; and the radicals $R^2$, $R^3$ and $R^5$ may be substituted by halogen atoms, especially fluorine and chlorine. The organosilicon compounds of the general formula (I) containing blocked isocyanate groups can be prepared by any desired processes.

The invention also provides a process for preparing the organosilicon compounds of the general formula (I), wherein organosilicon compounds containing isocyanate groups, of general formula (II)

$$(RO)_{3-n}(R^1)_n Si\text{—}CH_2\text{—}N=C=O \qquad (II)$$

are reacted with compounds HX, where R, R¹, X and n have the definitions described above. The preparation is carried out preferably in the presence of a basic or metallic catalysts. Preferred basic catalysts are alkali metal hydroxides and alkaline earth metal hydroxides, especially sodium hydroxide and potassium hydroxide.

The invention also provides a process for preparing the organosilicon compounds of the general formula (I), wherein organosilicon compounds containing chloroalkyl groups, of the general formula (III)

are reacted with compounds HX and salts of the general formula (IV)

where

M is an alkali metal or alkaline earth metal and m has the value 1 or 2, and

R, R¹, X and n have the definitions described above.

During the reaction it is possible not only for compounds of the general formulae (III), (IV), and HX to be present but also further, reaction-promoting substances.

Examples of blocking agents HX which can be eliminated from the organosilicon compounds of the general formula (I) on thermal exposure are ketone oximes such as 2-butanone oxime, methyl n-amyl ketone oxime, methyl isoamyl ketone oxime, cyclohexanone oxime, methyl isopropyl ketone oxime, methyl isobutyl ketone oxime, diisobutyl ketone oxime, methyl tert-butyl ketone oxime, diisopropyl ketone oxime, 2,2,6,6-tetramethylcyclohexanone oxime, or tetramethylcyclobutanedione monooxime; thiols such as thiophenol or 2-mercaptopyridine; CH-azidic compounds such as dimethyl malonate, diethyl malonate, methyl acetoacetate, ethyl acetoacetate, ethyl cyanoacetate, methyl cyanoacetate, or acetylacetone; amines such as methylphenylamine, diphenylamine, naphthylphenylamine, diisopropylamine, dicyclohexylamine, ethylisopropylamine, benzyl-tert-butylamine, tert-butylmethylamine, tert-butyliso-propylamine or 2,2,6,6-tetramethylpiperidine; or heterocyclic compounds such as imidazole, 2-isopropyl-imidazole, 3,5-dimethylpyrazole, and 5-methyl-2,3-dihydropyrazol-3-one.

Further blocking agents HX which can be eliminated thermally from the organosilicon compounds carrying blocked isocyanate groups are, for example, ε-caprolactam, γ-lactam, δ-lactam, N-methyl-acetamide, N-ethylacetamide, N-propylacetamide and N-isopropylacetamide.

Preferred blocking agents HX which can be thermally eliminated from silicon compounds of the general formula (I) are, for example, 2-butanone oxime, cyclohexanone oxime, methyl isopropyl ketone oxime, methyl isobutyl ketone oxime, methyl tert-butyl ketone oxime, diisopropyl ketone oxime, 2,2,6,6-tetramethylcyclohexanone oxime, tetramethyl-cyclobutanedione monooxime, thiophenol or 2-mercaptopyridine, dimethyl malonate, diethyl malonate, ethyl acetoacetate, ethyl cyanoacetate, acetylacetone, methylphenylamine, diphenylamine, diisopropylamine, dicyclohexylamine, benzyl-tert-butylamine, tert-butylmethylamine, tert-butyliso-propylamine, 2,2,6,6-tetramethylpiperidine, imidazole, 2-isopropylimidazole, 3,5-dimethylpyrazole, 5-methyl-2,3-dihydropyrazol-3-one, ε-caprolactam or N-methyl-acetamide.

Particularly preferred blocking agents HX which can be thermally eliminated from silicon compounds of the general formula (I) are 2-butanone oxime, dimethyl malonate, ethyl acetoacetate, diiso-propylamine, benzyl-tert-butylamine, tertbutyl-methylamine, tertbutylisopropylamine, 2-iso-propyl-imidazole, 3,5-dimethylpyrazole and ε-caprolactam.

The invention also provides for the use of the organosilicon compounds of the general formula (I) in coating compositions.

All of the symbols in the above formulae are defined independently of one another. In all formulae the silicon atom is tetravalent.

In the context of the present invention, unless indicated otherwise, all quantitative data and percentages are by weight, all temperatures are 20° C., and all pressures are 1.013 bar (abs.). All viscosities are determined at 25° C.

EXAMPLES

Example 1

Preparation of hexahydro-N-[(methoxy-dimethylsilyl)methyl]-2-oxo-1H-azepine-1-carboxamide A solution of 1.45 g of (isocyanatomethyl)methoxy-dimethylsilane and 1.13 g of ε-caprolactam in 25 ml of anhydrous dioxane was heated at reflux with stirring for 4 h. The solvent was subsequently removed under reduced pressure. This gave hexahydro-N-[(methoxydimethylsilyl)methyl]-2-oxo-1H-azepine-1-carboxamide in quantitative yield with a purity of >90% (analysis by ¹H NMR).

¹H NMR (500 MHz, chloroform-D) δ ppm 0.15-0.31 (m, 6H), 1.59-1.86 (m, 6H), 2.70 (dd, J=6.3 and 4.7 Hz, 2H), 2.82 (d, J=5.0 Hz, 2H), 3.48 (s, 3H), 3.99 (dd, J=5.0 and 3.8 Hz, 2H), 9.25 (s, 1H).

Example 2a

Preparation of N-[(methoxydimethylsilyl)-methyl]-2-oxo-1-pyrrolidinecarboxamide

Example 1 was repeated, with the modification that instead of ε-caprolactam 0.85 g of 2-pyrrolidinone was used. This gave N-[(methoxydimethylsilyl)methyl]-2-oxo-1-pyrrolidinecarboxamide in quantitative yield with a purity of >90% (analysis by ¹H NMR).

¹H NMR (500 MHz, chloroform-D) δ ppm 0.21 (s, 6H), 2.04 (tt, J=7.6 Hz, 2H), 2.61 (t, J=7.9 Hz, 2H), 2.83 (d, J=5.4 Hz, 2H), 3.49 (s, 3H), 3.87 (t, J=6.9 Hz, 2H), 8.38 (s, 1H).

Example 2b

Preparation of N-[(methoxydimethylsilyl)-methyl]-2-oxo-1-pyrrolidinecarboxamide

A mixture of 69.3 g of (chloromethyl)methoxydimethylsilane, 40.6 g of potassium cyanate and 42.6 g of 2-pyrrolidinone in 150 ml of anhydrous DMF was heated at 130° C. with stirring for 5 h. The solvent was then removed under reduced pressure. This gave N-[(methoxydimethylsilyl)methyl]-2-oxo-1-pyrrolidinecarboxamide in quantitative yield with a purity of >90% (analysis by ¹H NMR, see Example 2a).

Example 3a

Comparative Example for the Reaction of 2-butanone Oxime with (isocyanatomethyl)dimethoxy(methyl)silane without catalyst A stirred mixture conditioned at a temperature of 60° C. of 135 g of 2-butanone oxime was admixed over the course of 60 min with 250 g of (isocyanatomethyl)dimethoxy (methyl)silane. After the end of the addition the mixture was stirred at the temperature stated for a further 10 h. It was not possible to detect any N-{[dimethoxy(methyl)silyl] methyl}carbamoylmethyl ethyl ketone oxime (analysis by $^{29}$Si and $^1$H NMR).

Example 3b

Preparation of N-[(trimethoxysilyl)methyl]-carbamoylmethyl ethyl ketone oxime with metal catalysis A stirred mixture conditioned at a temperature of 80° C. of 86.1 g of 2-butanone oxime and 120 mg of "Borchi catalyst" (catalyst VP 0244 from Borchers GmbH, Langenfeld) was admixed over the course of 60 min with 150 g of (isocyanatomethyl)trimethoxysilane. After the end of the addition the mixture was stirred at the temperature stated for a further 60 min and excess 2-butanone oxime was removed by distillation. This gave N-[(trimethoxysilyl)methyl]carbamoylmethyl ethyl ketone oxime in quantitative yield with a purity of >95% (analysis by $^{29}$Si and $^1$H NMR).

$^1$H NMR (500 MHz, chloroform-D) δ ppm 1.05-1.17 (m, 3H), 1.86-2.02 (m, 3H), 2.20-2.51 (m, 2H), 2.73-3.03 (m, 2H) 3.45-3.77 (m, 9H), 6.15-6.55 (m, 1H).

Example 3c

Preparation of N-{[dimethoxy(methyl)silyl]-methyl}carbamoylmethyl ethyl ketone oxime with base catalysis A stirred mixture conditioned at a temperature of 60° C. of 135 g of 2-butanone oxime and 12.0 mg of potassium hydroxide was admixed over the course of 60 min with 250 g of (isocyanatomethyl)dimethoxy(methyl)silane. After the end of the addition the mixture was stirred at the stated temperature for a further 60 min. This gave N-{[dimethoxy (methyl)silyl]methyl}carbamoylmethyl ethyl ketone oxime in quantitative yield with a purity of >95% (analysis by $^{29}$Si and $^1$H NMR).

$^1$H NMR (500 MHz, benzene-D6) δ ppm 0.20 and 0.21 (2 s, 3H), 0.80 and 0.86 (2t, 3H, J=7.6 Hz), 1.53 and 1.65 (2s, 3H, J=59.9 Hz), 1.86 and 2.19 (2 q, 2J=7.9 Hz), 3.00 and 3.01 (2 d, 2H, J=5.3 Hz), 3.44 (s, 6H), 6.53-6.56 (2 br. s, 1H).

Example 3d

Preparation of N-{[dimethoxy(methyl)silyl]-methyl}carbamoyldimethyl ketone oxime with base catalysis Example 3c was repeated, with the modification that instead of 2-butanone oxime a solution of 113 g of acetone oxime in 400 ml of toluene was used. Distillative removal of the solvent under reduced pressure gave N-{[dimethoxy (methyl)silyl]-methyl}carbamoyldimethyl ketone oxime in quantitative yield with a purity of >95% (analysis by $^{29}$Si and $^1$H NMR).

$^1$H NMR (500 MHz, benzene-D6) δ ppm 0.21 (s, 3H), 1.41 (s, 3H), 1.56 (s, 3H), 3.03 (d, 2H, J=5.0 Hz), 3.43 (s, 6H), 6.47 (br. s, 1H).

Example 4a

Preparation of N-[(methoxydimethylsilyl)-methyl]-N',N'-diisopropylurea from (isocyanatomethyl)-methoxydimethylsilane A stirred mixture conditioned at a temperature of 80° C. of 10.1 g of N,N-diisopropylamine and 20.0 mg of "Borchi catalyst" was admixed over the course of 60 min with 14.5 g of (isocyanatomethyl)methoxydimethylsilane. After the end of the addition the mixture was stirred at the stated temperature for a further 60 min. This gave N-[(methoxy-dimethylsilyl)methyl]-N',N'-diisopropylurea after fractional distillation (b.p. 93-98° C./1 mbar) in 64% yield with a purity of >95% (analysis by $^{29}$Si and $^1$H NMR).

$^1$H NMR (300 MHz, chloroform-D) δ ppm 0.13 (s, 6H), 1.16 (d, J=6.9 Hz, 12H), 2.67 (d, J=4.7 Hz, 2H), 3.40 (s, 3H), 3.87 (sept, J=6.9 Hz, 2H), 4.16 (br. s, 1H).

Example 4b

Preparation of N-[(methoxydimethylsilyl)-methyl]-N',N'-diisopropylurea from (chloromethyl)-methoxydimethylsilane A mixture of 34.7 g of (chloromethyl)methoxydimethyl-silane, 20.3 g of potassium cyanate and 25.3 g of N,N-diisopropylamine in 75 ml of anhydrous DMF was heated at 130° C. with stirring for 5 h. The solvent was then removed under reduced pressure. This gave N-[(methoxydimethylsi-lyl)methyl]-N',N'-diisopropylurea after fractional distillation in 11% yield with a purity of >95% (analysis by $^1$H NMR, see Example 4a).

Example 4c

Preparation of N-{[dimethyl(methoxy)silyl]-methyl}-N',N'-diphenylurea

Example 4a was repeated, with the modification that instead of N,N-diisopropylamine a solution of 16.9 g of N,N-diphenylamine in 50 ml of toluene was used. Distillative removal of the solvent under reduced pressure and recrystallization of the residue from methyl tert-butyl ether gave N-{[dimethyl(methoxy)silyl]methyl}-N',N'-diphenylurea in quantitative yield with a purity of >95% (analysis by $^{29}$Si and $^1$H NMR).

$^1$H NMR (300 MHz, chloroform-D) δ ppm 0.11 (s, 6H), 2.74 (d, J=5.0 Hz, 2H), 3.33 (s, 3H), 4.45 (br. s, 1H), 7.11-7.40 (m, 10H).

Example 5

Preparation of N-[(methoxydimethylsilyl)-methyl-carbamoyl]morpholine

Example 4a was repeated, with the modification that instead of N,N-diisopropylamine 8.71 g of morpholine were used. This gave N-[(methoxydimethylsilyl)methyl-carbamoyl]morpholine after fractional distillation (b.p. 133-137° C./0.7 mbar) in 66% yield with a purity of >95% (analysis by $^{29}$Si and $^1$H NMR).

$^1$H NMR (300 MHz, chloroform-D) δ ppm 0.13 and 0.19 (s, 6H), 2.67 and 2.73 (d, J=4.7 Hz, 2H), 3.33 and 3.36 (t, J=5.0 Hz, 4H), 3.46 and 3.48 (s, 3H), 3.69 and 3.73 (t, J=5.0 Hz, 4H), 4.41 and 4.93 (br. s, 1H).

Example 6

Preparation of dimethyl 2-{[dimethoxy(methyl)silyl]methylcarbamoyl}malonate

A stirred mixture conditioned at a temperature of 30° C. of 6.74 g of dimethyl malonate and 90.0 mg of sodium methoxide (30% strength solution in methanol) was admixed dropwise with 8.06 g of (isocyanatomethyl)-dimethoxy(methyl)silane and the clear solution was stirred for 90 min. This gave dimethyl 2-{[dimethoxy(methyl)silyl]methylcarbamoyl}malonate after recrystallization from isohexane in 56% yield with a purity of >95% (analysis by $^1$H NMR).

$^1$H NMR (500 MHz, benzene-D6) δ ppm 0.20 (s, 3H), 2.98 (d, 2H, J=5.4 Hz), 3.26 (s, 6H), 3.41 (s, 6H), 4.45 (s, 1H).

Example 7

Preparation of 3,5-dimethyl-1-{[dimethoxy(methyl)silyl]methylcarbamoyl}pyrazole

A stirred solution conditioned at a temperature of 50° C. of 10.0 g of 3,5-dimethylpyrazole in 80 ml of ethyl acetate was admixed dropwise with 16.8 g of (isocyanatomethyl)dimethoxy(methyl)silane and the clear solution was stirred for 60 min. Distillative removal of the solvent under reduced pressure gave 3,5-dimethyl-1-{[dimethoxy(methyl)silyl]methylcarbamoyl}pyrazole in quantitative yield with a purity of >95% (analysis by $^{29}$Si and $^1$H NMR).

$^1$H NMR (500 MHz, benzene-D6) δ ppm 0.13 (s, 3H), 2.10 (s, 3H), 2.61 (s, 3H), 2.96 (d, J=5.4 Hz, 2H), 3.36 (s, 6H), 5.62 (s, 1H), 7.44 (br. s, 1H).

Example 8

Preparation of 2-isopropyl-1-{[dimethoxy-(methyl)silyl]methylcarbamoyl}imidazole A stirred solution conditioned at a temperature of 50° C. of 3.00 g of 2-isopropylimidazole in 50 ml of ethyl acetate was admixed dropwise with 4.39 g of (isocyanatomethyl)dimethoxy(methyl)silane and the mixture was stirred for 60 min. This gave 2-isopropyl-1-{[dimethoxy(methyl)silyl]-methylcarbamoyl}imidazole after filtration as a colorless solid in quantitative yield with a purity of >95% (analysis by $^{29}$Si and $^1$H NMR).

$^1$H NMR (500 MHz, benzene-D6) δ ppm 0.10 (s, 3H), 1.57 (d, J=6.6 Hz, 6H), 2.74 (d, J=5.0 Hz, 2H), 3.31 (s, 6H), 3.94 (sept, J=6.6 Hz, 1H), 4.92 (br. s, 1H), 6.55 (d, J=1.2 Hz, 1H), 7.04 (d, J=1.5 Hz, 1H).

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An organosilicon compound of the formula (I)

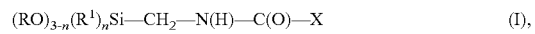

where
R each, independently, is a $C_1$-$C_{15}$ hydrocarbon radical or an acetyl radical,
$R^1$ each, independently, is a hydrogen atom or an Si—C-bonded $C_1$-$C_{20}$ hydrocarbon radical which is unsubstituted or substituted by —CN, —NCO, —NR$_2$, —COOH, —COOR, -halogen, -acryloyl, -epoxy, —SH, —OH or —CONR$_2$ in which one or more nonadjacent methylene units are optionally be replaced by groups —O—, —CO—, —COO—, —OCO—, or —OCOO—, —S—, or —NR—, and in which one or more nonadjacent methane units are optionally replaced by groups —N=, —N=N—, or —P=,
n has the value 0, 1 or 2,
X is a radical —NR$^2$R$^3$, —S—R$^5$, —C(H)(CO$_2$R$^5$)$_2$, or —O—N=CR$^2$R$^3$ and when X is —NR$^2$ R$^3$, R$^2$ and R$^3$ are not simultaneously hydrogen,
$R^2$, $R^3$ and $R^5$ each, independently, have the definitions of $R^1$, or are a cyclic, optionally branched hydrocarbon radical having 2-30 carbon atoms with at least 3 ring atoms, which are optionally functionalized by one or more groups —O—, —CO—, —COO—, —OCO—, —S—, =N—, —NR$^1$—, or —CONR$^1$—.

2. The organosilicon compound of claim 1, wherein R is a $C_1$-$C_8$ hydrocarbon radical or an acetyl radical.

3. The organosilicon compound of claim 1, wherein $R^1$ is a $C_1$-$C_3$ alkyl radical.

4. The organosilicon compound of claim 1 in which X is a residue of a compound selected from the group consisting of 2-butanone oxime, cyclohexanone oxime, methyl isopropyl ketone oxime, methyl isobutyl ketone oxime, methyl tert-butyl ketone oxime, diisopropyl ketone oxime, 2,2,6,6-tetramethylcyclohexanone oxime, tetramethylcyclobutanedione monooxime, thiophenol or 2-mercaptopyridine, dimethyl malonate, diethyl malonate, ethyl acetoacetate, ethyl cyanoacetate, acetylacetone, methylphenylamine, diphenylamine, diisopropylamine, dicyclohexylamine, benzyl-tert-butylamine, tert-butylmethylamine, tert-butyliso-propylamine, 2,2,6,6-tetramethylpiperidine, imidazole, 2-isopropylimidazole, 3,5-dimethyl-pyrazole, 5-methyl-2,3-dihydropyrazol-3-one, ε-caprolactam, and N-methylacetamide.

5. A process for preparing an organosilicon compound of the formula (I) of claim 1, comprising reacting organosilicon compounds containing isocyanate groups, of formula (II)

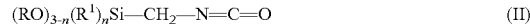

with compounds HX.

6. The process of claim 5, wherein the compound of formula HX is an oxime, and the reaction of HX with the compound of the formula (II) is catalyzed by a metal catalyst or a basic catalyst.

7. The process of claim 5 in which the blocking agent HX is selected from the group consisting of 2-butanone oxime, cyclohexanone oxime, methyl isopropyl ketone oxime, methyl isobutyl ketone oxime, methyl tert-butyl ketone oxime, diisopropyl ketone oxime, 2,2,6,6-tetramethylcyclohexanone oxime, tetramethylcyclobutanedione monooxime, thiophenol, 2-mercaptopyridine, dimethyl malonate, diethyl malonate, ethyl acetoacetate, ethyl cyanoacetate, acetylacetone, methylphenylamine, diphenylamine, diisopropylamine, dicyclohexylamine, benzyl-tert-butylamine, tert-butylmethylamine, tert-butyliso-propylamine, 2,2,6,6-tetramethylpiperidine, imidazole, 2-isopropylimidazole, 3,5-dimethyl-pyrazole, 5-methyl-2,3-dihydropyrazol-3-one, ε-caprolactam, and N-methylacetamide.

8. A process for preparing an organosilicon compound of the formula (I) of claim 1, comprising reacting organosilicon compound(s) containing chloroalkyl groups, of the formula (III)

$(RO)_{3-n}(R^1)_n Si-CH_2-Cl$ (III)

with compounds HX and salts of the formula (IV)

$M(OCN)_m$ (IV)

where
M is an alkali metal or alkaline earth metal and
m has the value 1 when m is an alkali metal and 2 when M is an alkaline earth metal.

9. A process for eliminating a blocking agent HX from a compound of the formula I of claim 1, comprising heating the compound to a temperature in the range of 30-250° C.

10. In a coating composition in which an isocyanate reacts with an isocyanate-reactive group, the improvement comprising employing as at least a portion of the isocyanate, a blocked isocyanate of the formula (I) of claim 1, and heating to an elevated temperature to thermally eliminate the blocking group, generating an —NCO group.

* * * * *

UNITED STATES PATENT AND TRADEMARK OFFICE
CERTIFICATE OF CORRECTION

| | | |
|---|---|---|
| PATENT NO. | : 7,368,586 B2 | Page 1 of 1 |
| APPLICATION NO. | : 11/668207 | |
| DATED | : May 6, 2008 | |
| INVENTOR(S) | : Jürgen Pfeiffer et al. | |

It is certified that error appears in the above-identified patent and that said Letters Patent is hereby corrected as shown below:

Column 8, Line 17, Claim 1,

Delete "methane" and insert -- methine --.

Signed and Sealed this

Twenty-ninth Day of July, 2008

JON W. DUDAS
*Director of the United States Patent and Trademark Office*